United States Patent
Simpson et al.

(10) Patent No.: US 7,108,778 B2
(45) Date of Patent: Sep. 19, 2006

(54) ELECTROCHEMICAL SENSORS INCLUDING ELECTRODE SYSTEMS WITH INCREASED OXYGEN GENERATION

(75) Inventors: Peter C. Simpson, Del Mar, CA (US); Paul Goode, Murrieta, CA (US); Mark A. Tapsak, Orangeville, PA (US); Victoria Carr-Brendel, Pleasanton, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 10/897,377

(22) Filed: Jul. 21, 2004

(65) Prior Publication Data

US 2005/0051440 A1    Mar. 10, 2005

Related U.S. Application Data

(60) Provisional application No. 60/490,208, filed on Jul. 25, 2003.

(51) Int. Cl.
*G01N 27/327* (2006.01)

(52) U.S. Cl. .............. 205/778; 205/777.5; 204/403.1; 204/403.09; 204/403.14

(58) Field of Classification Search ............ 204/403.01–403.15; 205/777.5, 778
See application file for complete search history.

(56) References Cited

U.S. PATENT DOCUMENTS

| | | | |
|---|---|---|---|
| 4,255,500 A | 3/1981 | Hooke | |
| 4,324,257 A * | 4/1982 | Albarda et al. ............. | 600/357 |
| 4,374,013 A | 2/1983 | Enfors | |
| 4,388,166 A | 6/1983 | Suzuki et al. | |
| 4,431,004 A | 2/1984 | Bessman et al. | |
| 4,671,288 A | 6/1987 | Gough | |
| 4,703,756 A | 11/1987 | Gough et al. | |
| 4,721,677 A | 1/1988 | Clark, Jr. | |
| 4,757,022 A | 7/1988 | Shults et al. | |
| 4,776,944 A | 10/1988 | Janata et al. | |
| 4,781,798 A | 11/1988 | Gough | |
| 4,890,620 A | 1/1990 | Gough | |
| 4,994,167 A | 2/1991 | Shults et al. | |
| 5,030,333 A | 7/1991 | Clark, Jr. | |
| 5,140,985 A | 8/1992 | Schroeder et al. | |

(Continued)

FOREIGN PATENT DOCUMENTS

EP    0396788 A1 *    11/1990

(Continued)

OTHER PUBLICATIONS

Abel, P. U.; von Woedtke, T. Biosensors for in vivo glucose measurement: can we cross the experimental stage. Biosens Bioelectron 2002, 17, 1059-1070.

(Continued)

*Primary Examiner*—Alex Noguerola
(74) *Attorney, Agent, or Firm*—Knobbe, Martens, Olson & Bear, LLP

(57) ABSTRACT

The present invention relates generally to systems and methods for increasing oxygen generation in electrochemical sensors in order to overcome the oxygen limitations. The preferred embodiments employ electrode systems with at least two electrodes in relatively close proximity to each other; wherein at least one electrode is configured to generate oxygen and at least one other electrode is configured to sense an analyte or a product of a reaction indicative of the concentration of analyte. The oxygen generated by the oxygen-generating electrode is available to the catalyst within a membrane system and/or the counter electrode, thereby enabling the electrochemical sensors of the preferred embodiments to function even during ischemic conditions.

51 Claims, 7 Drawing Sheets

U.S. PATENT DOCUMENTS

| | | |
|---|---|---|
| 5,198,771 A | 3/1993 | Fidler et al. |
| 5,411,647 A | 5/1995 | Johnson et al. |
| 5,431,160 A | 7/1995 | Wilkins |
| 5,494,562 A | 2/1996 | Maley et al. |
| 5,496,453 A | 3/1996 | Uenoyama et al. |
| 5,571,395 A | 11/1996 | Park et al. |
| 5,605,152 A | 2/1997 | Slate et al. |
| 5,607,565 A * | 3/1997 | Azarnia et al. ........ 204/403.09 |
| 5,628,890 A | 5/1997 | Carter et al. |
| 5,653,863 A | 8/1997 | Genshaw et al. |
| 5,686,829 A | 11/1997 | Girault |
| 5,795,774 A | 8/1998 | Matsumoto et al. |
| 5,914,026 A | 6/1999 | Blubaugh, Jr. et al. |
| 5,964,993 A | 10/1999 | Blubaugh et al. |
| 5,965,380 A | 10/1999 | Heller et al. |
| 5,985,129 A | 11/1999 | Gough et al. |
| 5,989,409 A * | 11/1999 | Kurnik et al. .............. 205/792 |
| 5,999,848 A | 12/1999 | Gord et al. |
| 6,001,067 A | 12/1999 | Shults et al. |
| 6,081,735 A | 6/2000 | Diab et al. |
| 6,081,736 A | 6/2000 | Colvin et al. |
| 6,088,608 A | 7/2000 | Schulman et al. |
| 6,119,028 A | 9/2000 | Schulman et al. |
| 6,120,676 A | 9/2000 | Heller et al. |
| 6,122,536 A | 9/2000 | Sun et al. |
| 6,134,461 A | 10/2000 | Say et al. |
| 6,141,573 A | 10/2000 | Kurnik et al. |
| 6,144,869 A | 11/2000 | Berner et al. |
| 6,189,536 B1 | 2/2001 | Martinez et al. |
| 6,212,416 B1 | 4/2001 | Ward et al. |
| 6,274,285 B1 | 8/2001 | Gries et al. |
| 6,300,002 B1 | 10/2001 | Webb et al. |
| 6,309,526 B1 * | 10/2001 | Fujiwara et al. ........ 204/403.14 |
| 6,325,979 B1 | 12/2001 | Hahn et al. |
| 6,329,161 B1 | 12/2001 | Heller et al. |
| 6,356,776 B1 | 3/2002 | Berner et al. |
| 6,400,974 B1 | 6/2002 | Lesho |
| 6,466,810 B1 | 10/2002 | Ward et al. |
| 6,512,939 B1 | 1/2003 | Colvin et al. |
| 6,514,718 B1 | 2/2003 | Heller et al. |
| 6,542,765 B1 | 4/2003 | Guy et al. |
| 6,546,268 B1 | 4/2003 | Ishikawa et al. |
| 6,551,496 B1 | 4/2003 | Moles et al. |
| 6,595,919 B1 | 7/2003 | Berner et al. |
| 6,615,078 B1 | 9/2003 | Burson et al. |
| 6,618,934 B1 | 9/2003 | Feldman et al. |
| 6,702,857 B1 | 3/2004 | Brauker et al. |
| 6,793,802 B1 * | 9/2004 | Lee et al. ................ 205/777.5 |
| 6,809,507 B1 | 10/2004 | Morgan et al. |
| 6,862,465 B1 | 3/2005 | Shults et al. |
| 6,891,317 B1 | 5/2005 | Pei et al. |
| 6,892,085 B1 | 5/2005 | McIvor et al. |
| 2003/0032874 A1 | 2/2003 | Rhodes et al. |
| 2003/0050546 A1 | 3/2003 | Desai et al. |
| 2004/0106857 A1 | 6/2004 | Gough |
| 2004/0219664 A1 | 11/2004 | Heller et al. |
| 2005/0027180 A1 | 2/2005 | Goode et al. |
| 2005/0027181 A1 | 2/2005 | Goode et al. |
| 2005/0027462 A1 | 2/2005 | Goode et al. |
| 2005/0027463 A1 | 2/2005 | Goode et al. |
| 2005/0031689 A1 | 2/2005 | Shults et al. |
| 2005/0033132 A1 | 2/2005 | Shults et al. |
| 2005/0043598 A1 | 2/2005 | Goode et al. |
| 2005/0051427 A1 | 3/2005 | Brauker et al. |
| 2005/0054909 A1 | 3/2005 | Petisce et al. |
| 2005/0056552 A1 | 3/2005 | Simpson et al. |
| 2005/0090607 A1 | 4/2005 | Tapsak et al. |
| 2005/0112169 A1 | 5/2005 | Brauker et al. |
| 2005/0192557 A1 | 9/2005 | Brauker et al. |

FOREIGN PATENT DOCUMENTS

| | | |
|---|---|---|
| EP | 0539625 A1 * | 5/1993 |
| EP | 1153571 A1 | 11/2001 |
| FR | 2 656 423 | 6/1991 |
| GB | 1 442 303 | 7/1976 |
| JP | 62083849 | 4/1987 |
| WO | WO 94/22367 | 10/1994 |
| WO | WO 99/58051 | 11/1999 |
| WO | WO 01/68901 A2 | 9/2001 |
| WO | WO 01/88524 A1 | 11/2001 |
| WO | WO 04/021877 A1 | 3/2004 |

OTHER PUBLICATIONS

Baker, et al. 1993. Dynamic concentration challenges for biosensor characterization. *Biosensors & Bioelectronics*, 8:433-441.

Bindra, et al. 1989. Pulsed amperometric detection of glucose in biological fluids at a surface-modified gold electrode. *Anal Chem*, 61:2566-2570.

Bisenberger, et al. 1995. A triple-step potential waveform at enzyme multisensors with thick-film gold electrodes for detection of glucose and sucrose. *Sensors and Actuators*, B 28:181-189.

Bott, A. W. 1997. A comparison of cyclic voltammetry and cyclic staircase voltammetry. *Current Separations*, 16(1):23-26.

Bott, A. 1998. Electrochemical methods for the determination of glucose. *Current Separations*, 17(1):25-31.

Choleau, et al. 2002. Calibration of a subcutaneo amperometric glucose sensor. Part 1. Effect of measurement uncertainties on the determination of sensor sensitivity and background current. *Biosensors and Bioelectronics*, 17:641-646.

Dixon, et al. 2002. Characterization in vitro and in vivo of the oxygen dependence of an enzyme/polymer biosensor for monitoring brain glucose. *Journal of Neuroscience Methods*, 119:135-142.

Gilligan, B. C.; Shults, M.; Rhodes, R. K.; Jacobs, P. G.; Brauker, J. H.; Pintar, T. J.; Updike, S. J. Feasibility of continuo long-term glucose monitoring from a subcutaneous glucose sensor in humans. Diabetes Technol Ther 2004, 6, 378-386.

Hall, et al. 1998. Electrochemical oxidation of hydrogen peroxide at platinum electrodes. Part 1. An adsorption-controlled mechanism. *Electrochimica Acta*, 43(5-6):579-588.

Hall, et al. 1998. Electrochemical oxidation of hydrogen peroxide at platinum electrodes. Part II: Effect of potential. *Electrochimica Acta*, 43(14-15):2015-2024.

Hall, et al. 1999. Electrochemical oxidation of hydrogen peroxide at platinum electrodes. Part III: Effect of temperature. *Electrochimica Acta*, 44:2455-2462.

Hall, et al. 1999. Electrochemical oxidation of hydrogen peroxide at platinum electrodes. Part IV: Phosphate buffer dependence. *Electrochimica Acta*, 44:4573-4582.

Hall, et al. 2000. Electrochemical oxidation of hydrogen peroxide at platinum electrodes. Part V: Inhibition by chloride. *Electrochimica Acta*, 45:3573-3579.

Heller, A. Implanted electrochemical glucose sensors for the management of diabetes. Annu Rev Biomed Eng 1999, 1, 153-175.

Hitchman, M. L. 1978. "Measurement of Dissolved Oxygen." In Elving, et al. (Eds.). Chemical Analysis, vol. 49, Chap. 3, pp. 34-49, 59-123. New York: John Wiley & Sons.

Huang, C., O'Grady, W.E.; Yeager, E. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116, Aug. 1975.

Jablecki, et al. 2000. Simulations of the frequency response of implantable glucose sensors. *Analytical Chemistry*, 72:1853-1859.

Jaremko, et al. 1998. Advances toward the implantable artificial pancreas for treatment of diabetes. *Diabetes Care*, 21(3):444-450.

Jensen, et al. 1997. Fast wave forms for pulsed electrochemical detection of glucose by incorporation of reductive desorption of oxidation products. *Analytical Chemistry*, 69(9):1776-1781.

Kang, S. K.; Jeong, R. A.; Park, S.; Chung, T. D.; Park, S.; Kim, H. C. In vitro and short-term in vivo characteristics of a Kel-F thin film modified glucose sensor. Anal Sci 2003, 19, 1481-1486.

Kraver, K.; Gutha , M. R.; Strong, T.; Bird, P.; Cha, G.; Hoeld, W.; Brown, R. A mixed-signal sensor interface microinstrument. Sensors and Actuators A: Physical 2001, 91, 266-277.

LaCourse, et al. 1993. Optimization of waveforms for pulsed amperometric detection of carbohydrates based on pulsed voltammetry. *Analytical Chemistry*, 65:50-52.

Lerner, et al. 1984. An implantable electrochemical glucose sensor. *Ann. N. Y. Acad. Sci.*, 428:263-278.

Leypoldt, et al. 1984. Model of a two-substrate enzyme electrode for glucose. *Anal. Chem.*, 56:2896-2904.

McGrath, M. J.; Iwuoha, E. I.; Diamond, D.; Smyth, M. R. The use of differential measurements with a glucose biosensor for interference compensation during glucose determinations by flow injection analysis. Biosens Bioelectron 1995, 10, 937-943.

Mernoli, A.; Annesini, M. C.; Mascini, M.; Papale , S.; Petralito, S. A comparison between different immobilised glucoseoxidase-based electrodes. J Pharm Biomed Anal 2002, 29, 1045-1052.

Neuburger, et al. 1987. Pulsed amperometric detection of carbohydrates at gold electrodes with a two-step potential waveform. *Anal. Chem.*, 59:150-154.

Postlethwaite, et al. 1996. Interdigitated array electrode as an alternative to the rotated ring-disk electrode for determination of the reaction products of dioxygen reduction. *Analytical Chemistry*, 68:2951-2958.

Rhodes, et al. 1994. Prediction of pocket-portable and implantable glucose enzyme electrode performance from combined species permeability and digital simulation analysis. *Analytical Chemistry*, 66(9):1520-1529.

Sansen, et al. 1990. A smart sensor for the voltammetric measurement of oxygen or glucose concentrations. *Sensors and Actuators*, B 1:298-302.

Wang, X.; Pardue, H. L. Improved ruggedness for membrane-based amperometric sensors using a pulsed amperometric method. Anal Chem 1997, 69, 4482-4489.

Ward, W. K.; Wood, M. D.; Troupe, J. E. Understanding Spontaneous Output Fluctuations of an Amperometric Glucose Sensor: Effect of Inhalation Anesthesia and e of a Nonenzyme Containing Electrode. ASAIO Journal 2000, 540-546.

Ward, et al. 2000. Rise in background current over time in a subcutaneous glucose sensor in the rabbit: Relevance to calibration and accuracy. *Biosensors & Bioelectronics*, 15:53-61.

Ward et al. 2002. A new amperometric glucose microsensor: In vitro and short-term in vivo evaluation. *Biosensors & Bioelectronics*, 17:181-189.

Wilkins, et al. 1995. Integrated implantable device for long-term glucose monitoring. *Biosens. Bioelectron.*, 10:485-494.

Wientjes, K. J. C. Development of a glucose sensor for diabetic patients. 2000.

Wilson, et al. 1992. Progress toward the development of an implantable sensor for glucose. *Clin. Chem.*, 38(9):1613-1617.

Wu, et al. 1999. *In situ* electrochemical oxygen generation with an immunoisolation device. *Ann. N.Y. Acad. Sci.*, 875:105-125.

Zhang, et al. 1994. Elimination of the acetaminophen interference in an implantable glucose sensor. *Analytical Chemistry*, 66(7):1183-1188.

U.S. Appl. No. 09/447,227, filed Nov. 22, 1999.
U.S. Appl. No. 10/838,658, filed May 3, 2004.
U.S. Appl. No. 10/838,909, filed May 3, 2004.
U.S. Appl. No. 10/838,912, filed May 3, 2004.
U.S. Appl. No. 10/885,476, filed Jul. 6, 2004.
U.S. Appl. No. 10/896,312, filed Jul. 21, 2004.

* cited by examiner

FIG. 1A – PRIOR ART

ELECTROCHEMICAL SENSORS INCLUDING ELECTRODE SYSTEMS WITH INCREASED OXYGEN GENERATION

RELATED APPLICATION

This application claims the benefit of priority under 35 U.S.C. § 119(e) to U.S. Provisional Application No. 60/490,208, filed Jul. 25, 2003, the contents of which are hereby incorporated herein by reference in their entirety.

FIELD OF THE INVENTION

The present invention relates generally to systems and methods for increasing oxygen generation in electrochemical sensors.

BACKGROUND OF THE INVENTION

Electrochemical sensors are useful in chemistry and medicine to determine the presence or concentration of a biological analyte. Such sensors are useful, for example, to monitor glucose in diabetic patients and lactate during critical care events.

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which causes an array of physiological derangements (kidney failure, skin ulcers, or bleeding into the vitreous of the eye) associated with the deterioration of small blood vessels. A hypoglycemic reaction (low blood sugar) is induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically employs uncomfortable finger pricking methods. Due to the lack of comfort and convenience, a diabetic normally only measures his or her glucose level two to four times per day. Unfortunately, these time intervals are spread apart so far that the diabetic likely finds out too late, sometimes incurring dangerous side effects, of a hyperglycemic or hypoglycemic condition. In fact, it is not only unlikely that a diabetic will take a timely SMBG value, but additionally the diabetic will not know if their blood glucose value is going up (higher) or down (lower) based on conventional methods.

Consequently, a variety of transdermal and implantable electrochemical sensors are being developed for continuous detecting and/or quantifying of blood glucose values. Many implantable glucose sensors suffer from complications within the body and provide only short-term or less-than-accurate sensing of blood glucose. Similarly, transdermal sensors have problems in accurately sensing and reporting back glucose values continuously over extended periods of time. Some efforts have been made to obtain blood glucose data from implantable devices and retrospectively determine blood glucose trends for analysis; however these efforts do not aid the diabetic in determining real-time blood glucose information. Some efforts. have also been made to obtain blood glucose data from transdermal devices for prospective data analysis. However similar problems have occurred.

SUMMARY OF THE PREFERRED EMBODIMENTS

Sensors that can provide accurate, real-time information under ischemic conditions are therefore desirable.

Accordingly, in a first embodiment, an electrochemical sensor for determining a presence or a concentration of an analyte in a fluid is provided, the sensor including a membrane system including an enzyme that reacts with the analyte; a first working electrode including a conductive material, wherein the first working electrode is configured to measure a product of the reaction of the enzyme with the analyte; and an auxiliary electrode including a conductive material, wherein the auxiliary electrode is configured to generate oxygen, wherein the auxiliary electrode is located at a proximity to the first working electrode such that oxygen generated at the auxiliary electrode diffuses to the enzyme at a location substantially above the first working electrode.

In an aspect of the first embodiment, a distance between the first working electrode and the auxiliary electrode is from about 0.5 to about 1000 microns.

In an aspect of the first embodiment, a distance between the first working electrode and the auxiliary electrode is from about 10 to about 100 microns.

In an aspect of the first embodiment, a distance between the first working electrode and the auxiliary electrode is about 50 microns.

In an aspect of the first embodiment, at least one of the first working electrode and the auxiliary electrode is configured in a pattern selected from the group consisting of spiral, concentric, adjacent, interdigitated, and sandwiched.

In an aspect of the first embodiment, at least one of the first working electrode and the auxiliary electrode is formed by a process selected from the group consisting of thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, and laser cutting.

In an aspect of the first embodiment, the first working electrode includes a sensing electrode, and wherein the auxiliary electrode includes an oxygen-generating electrode.

In an aspect of the first embodiment, the electrochemical sensor further includes a counter electrode, wherein the counter electrode is situated in proximity to the auxiliary electrode such that oxygen generated by the auxiliary electrode diffuses to the counter electrode.

In an aspect of the first embodiment, the electrochemical sensor further includes at least one additional auxiliary electrode including a conductive material and configured to generate oxygen.

In an aspect of the first embodiment, the additional auxiliary electrode is configured to substantially surround the first working electrode.

In a second embodiment, an electrochemical sensor for determining a presence or a concentration of an analyte in a fluid is provided, the sensor including a membrane system including an enzyme that reacts with the analyte; a first working electrode including a conductive material, wherein the first working electrode is configured to measure a product of the reaction of the enzyme with the analyte; and an auxiliary electrode including a conductive material, wherein the auxiliary electrode is configured to generate oxygen; and a counter electrode including a conductive material, wherein the counter electrode is configured to reduce oxygen so as to balance current being generated by the first working electrode, wherein the auxiliary electrode is located at a proximity to the counter electrode such that oxygen generated at the auxiliary electrode diffuses to the counter electrode to be reduced thereby.

In an aspect of the second embodiment, a distance between the auxiliary electrode and the counter electrode is from about 0.5 microns to about 1000 microns.

In an aspect of the second embodiment, a distance between the auxiliary electrode and the counter electrode is from about 10 microns to about 100 microns.

In an aspect of the second embodiment, a distance between the auxiliary electrode and the counter electrode is about 50 microns.

In an aspect of the second embodiment, at least one of the working electrode and the counter electrode is configured in a pattern selected from the group consisting of spiral, concentric, adjacent, interdigitated, and sandwiched.

In an aspect of the second embodiment, at least one of the working electrode and the counter electrode is formed by a process selected from the group consisting of thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, and laser cutting.

In an aspect of the second embodiment, the first working electrode includes a sensing electrode, and wherein the auxiliary electrode includes an oxygen-generating electrode.

In an aspect of the second embodiment, the electrochemical sensor further includes an additional working electrode including a conductive material, wherein the additional working electrode is configured to measure an additional analyte or is configured to function as a baseline-subtracting electrode.

In an aspect of the second embodiment, the electrochemical sensor further includes at least one additional working electrode including a conductive material and configured to generate oxygen.

In an aspect of the second embodiment, the additional working electrode is configured to substantially surround the first working electrode.

In a third embodiment, a method for generating oxygen for use at an electrochemical analyte sensor is provided, the method including providing a membrane system including an enzyme that reacts with the analyte; providing a first working electrode including a conductive material; measuring a product of a reaction of the enzyme with the analyte at the first working electrode, wherein a concentration of the product is indicative of a concentration of the analyte; providing an auxiliary electrode including a conductive material; and generating oxygen at the auxiliary electrode, wherein the auxiliary electrode is configured such that the oxygen generated at the auxiliary electrode diffuses toward the enzyme at a location substantially above the first working electrode.

In an aspect of the third embodiment, the enzyme is selected from the group consisting of glucose oxidase, amino acid oxidase, alcohol oxidase, galactose oxidase, lactate oxidase, and cholesterol oxidase.

In an aspect of the third embodiment, the analyte is selected from the group consisting of glucose, amino acid, alcohol, galactose, lactate, and cholesterol.

In a fourth embodiment, a method for generating oxygen for use at an electrochemical analyte sensor is provided, the method including providing an electrochemical sensor including a sensing electrode and an auxiliary electrode; measuring an analyte at the sensing electrode; and generating oxygen at the auxiliary electrode, wherein the electrochemical sensor includes an oxygen-utilizing source, and wherein the oxygen generated by the auxiliary electrode diffuses to the oxygen-utilizing source.

In an aspect of the fourth embodiment, the oxygen-utilizing source includes an enzyme.

In an aspect of the fourth embodiment, the oxygen-utilizing source includes a counter electrode.

BRIEF DESCRIPTION OF THE DRAWINGS

FIG. 1A is an exploded perspective view of one exemplary embodiment of a prior art implantable glucose sensor that utilizes a conventional electrode system.

DETAILED DESCRIPTION OF THE PREFERRED EMBODIMENT

Figure 1B:
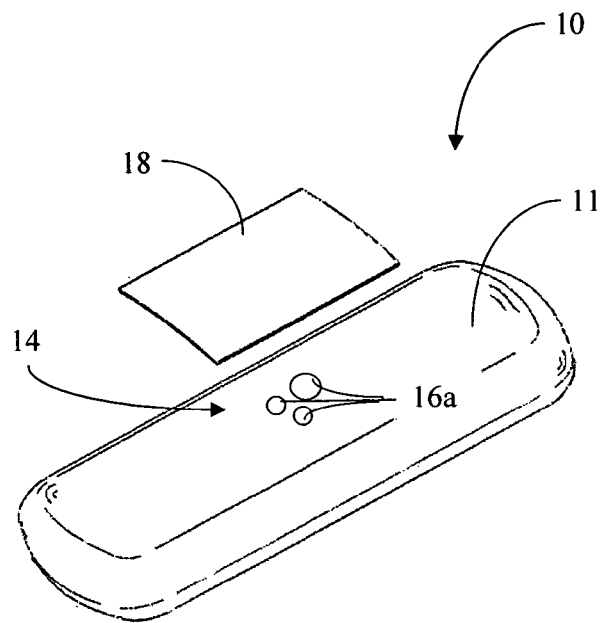
FIG. 1B is an exploded perspective view of one exemplary embodiment of an implantable glucose sensor that utilizes an electrode system of the preferred embodiments.

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the preferred embodiments, a number of terms are defined below.

The term "analyte" as used herein is a broad term and is used in its ordinary sense, including, without limitation, to refer to a substance or chemical constituent in a biological fluid (for example, blood, interstitial fluid, cerebral spinal fluid, lymph fluid or urine) that can be analyzed. Analytes can include naturally occurring substances, artificial substances, metabolites, and/or reaction products. In some embodiments, the analyte for measurement by the sensing regions, devices, and methods is glucose. However, other analytes are contemplated as well, including but not limited to acarboxyprothrombin; acylcarnitine; adenine phosphoribosyl transferase; adenosine deaminase; albumin; alphafetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, glucose-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, antinuclear antibody, anti-zeta antibody, arbovirus, Aujeszky's disease virus, dengue virus, *Dracunculus medinensis, Echinococcus granulosus, Entamoeba histolytica,* enterovirus, *Giardia duodenalisa, Helicobacter pylori,* hepatitis B virus, herpes virus, HIV-1, IgE (atopic disease), influenza virus, *Leishmania donovani,* leptospira, measles/mumps/rubella, *Mycobacterium leprae, Mycoplasma pneumoniae,* Myoglobin, *Onchocerca volvulus,* parainfluenza virus, *Plasmodium falciparum,* poliovirus, *Pseudomonas aeruginosa,* respiratory syncytial virus, rickettsia (scrub typhus), *Schistosoma mansoni, Toxoplasma gondii, Trepenoma pallidium, Trypanosoma cruzi/rangeli,* vesicular stomatis virus, *Wuchereria bancrofti,* yellow fever virus); specific antigens (hepatitis B virus, HIV-1); succinylacetone; sulfadoxine; theophylline; thyrotropin (TSH); thyroxine (T4); thyroxinebinding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids can also constitute analytes in certain embodiments. The analyte can be naturally present in the biological fluid, for example, a metabolic product, a hormone, an antigen, an antibody, and the like. Alternatively, the analyte can be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3 MT), 3,4-dihydroxyphenylacetic acid (DOPAC), homovanillic acid (HVA), 5-hydroxytryptamine (5HT), and 5-hydroxyindoleacetic acid (FHIAA).

The terms "operable connection," "operably connected," and "operably linked" as used herein are broad terms and are used in their ordinary sense, including, without limitation, one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably linked" to the electronic circuitry.

The term "host" as used herein is a broad term and is used in its ordinary sense, including, without limitation, mammals, particularly humans.

The terms "electrochemically reactive surface" and "electroactive surface" as used herein are broad terms and are used in their ordinary sense, including, without limitation, the surface of an electrode where an electrochemical reaction takes place. As an example, a working electrode measures hydrogen peroxide produced by the enzyme catalyzed reaction of the analyte being detected, creating an electric current (for example, detection of glucose analyte utilizing glucose oxidase produces $H_2O_2$ as a by product, $H_2O_2$ reacts with the surface of the working electrode producing two protons ($2H^+$), two electrons ($2e^-$) and one molecule of oxygen ($O_2$) which produces the electronic current being detected). In the case of the counter electrode, a reducible species, for example, $O_2$ is reduced at the electrode surface in order to balance the current generated by the working electrode.

The term "sensing region" as used herein is a broad term and is used in its ordinary sense, including, without limitation, the region of a monitoring device responsible for the detection of a particular analyte. The sensing region generally comprises a nonconductive body, a working electrode, a reference electrode, and/or a counter electrode (optional) passing through and secured within the body forming electrochemically reactive surfaces on the body, an electronic connective means at another location on the body, and a multi-domain membrane affixed to the body and covering the electrochemically reactive surface.

The terms "raw data stream" and "data stream," as used herein, are broad terms and are used in their ordinary sense, including, without limitation, an analog or digital signal directly related to the measured glucose concentration from the glucose sensor. As an example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts," as used herein, is a broad term and is used in its ordinary sense, including, without limitation, a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The term "electrical potential," as used herein, is a broad term and is used in its ordinary sense, including, without limitation, the electrical potential difference between two points in a circuit which is the cause of the flow of a current.

The term "ischemia," as used herein, is a broad term and is used in its ordinary sense, including, without limitation, local and temporary deficiency of blood supply due to obstruction of circulation to a part (for example, sensor). Ischemia can be caused by mechanical obstruction (for example, arterial narrowing or disruption) of the blood supply, for example.

The term "system noise," as used herein, is a broad term and is used in its ordinary sense, including, without limitation, unwanted electronic or diffusion-related noise which can include Gaussian, motion-related, flicker, kinetic, or other white noise, for example.

The terms "signal artifacts" and "transient non-glucose related signal artifacts that have a higher amplitude than system noise," as used herein, are broad terms and are used in their ordinary sense, including, without limitation, signal noise that is caused by substantially non-glucose reaction rate-limiting phenomena, such as ischemia, pH changes, temperature changes, pressure, and stress, for example. Signal artifacts, as described herein, are typically transient and are characterized by a higher amplitude than system noise.

The terms "low noise," as used herein, is a broad term and is used in its ordinary sense, including, without limitation, noise that substantially decreases signal amplitude.

The terms "high noise" and "high spikes," as used herein, are broad terms and are used in their ordinary sense, including, without limitation, noise that substantially increases signal amplitude.

The phrase "distal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell disruptive domain is positioned farther from the sensor, then that domain is distal to the sensor.

The phrase "proximal to" as used herein is a broad term and is used in its ordinary sense, including, without limitation, the spatial relationship between various elements in comparison to a particular point of reference. For example, some embodiments of a device include a membrane system having a cell disruptive domain and a cell impermeable domain. If the sensor is deemed to be the point of reference and the cell impermeable domain is positioned nearer to the sensor, then that domain is proximal to the sensor.

As employed herein, the following abbreviations apply: Eq and Eqs (equivalents); mEq (milliequivalents); M (molar); mM (millimolar) μM (micromolar); N (Normal); mol (moles); mmol (millimoles); μmol (micromoles); nmol (nanomoles); g (grams); mg (milligrams); μg (micrograms); Kg (kilograms); L (liters); mL (milliliters); dL (deciliters); μL (microliters); cm (centimeters); mm (millimeters); μm (micrometers); nm (nanometers); h and hr (hours); min. (minutes); s and sec. (seconds); ° C. (degrees Centigrade).

Overview

The preferred embodiments relate to the use of an electrochemical sensor that measures a concentration of an analyte of interest or a substance indicative of the concentration or presence of the analyte in fluid. In some embodiments, the sensor is a continuous device, for example a subcutaneous, transdermal, or intravascular device. In some embodiments, the device can analyze a plurality of intermittent blood samples.

The sensor can use any known method, including invasive, minimally invasive, and non-invasive sensing techniques, to provide an output signal indicative of the concentration of the analyte of interest. The sensor can be of the type that senses a product or reactant of an enzymatic reaction between an analyte and an enzyme in the presence of oxygen as a measure of the analyte in vivo or in vitro. Such a sensor typically comprises a membrane surrounding the enzyme through which a bodily fluid passes and in which an analyte within the bodily fluid reacts with an enzyme in the presence of oxygen to generate a product. The product is then measured using electrochemical methods and thus the output of an electrode system functions as a measure of the analyte. In some embodiments, the sensor can use amperometric, coulometric, conductimetric, and/or potentiometric techniques for measuring the analyte. In some embodiments, the electrode system can be used with any of a variety of known in vitro or in vivo analyte sensors or monitors.

FIG. 1A is an exploded perspective view of one exemplary embodiment of a prior art implantable glucose sensor 10 that utilizes a conventional electrode system 16a. In this exemplary embodiment, a body 12 with a sensing region 14 includes an electrode system 16a and sensor electronics, which are described in more detail with reference to FIG. 2.

In this embodiment, the electrode system 16a is operably connected to the sensor electronics (FIG. 2) and includes electroactive surfaces, which are covered by a membrane system 18. The membrane system 18 is disposed over the electroactive surfaces of the electrode system 16a and provides one or more of the following functions: 1) protection of the exposed electrode surface from the biological environment (cell impermeable domain); 2) diffusion resistance (limitation) of the analyte (resistance domain); 3) a catalyst for enabling an enzymatic reaction (enzyme domain); 4) limitation or blocking of interfering species (interference domain); and/or 5) hydrophilicity at the electrochemically reactive surfaces of the sensor interface (electrolyte domain), for example, such as described in co-pending U.S. patent application Ser. No. 10/838,912, filed May 3, 2004 and entitled "IMPLANTABLE ANALYTE SENSOR," which is incorporated herein by reference in its entirety. The membrane system can be attached to the sensor body 12 by mechanical or chemical methods such as described in co-pending U.S. patent application MEMBRANE ATTACHMENT and U.S. patent application Ser. No. 10/838,912 filed May 3, 2004 and entitled, "IMPLANTABLE ANALYTE SENSOR", which are incorporated herein by reference in their entirety.

In the embodiment of FIG. 1A, the electrode system 16a includes three electrodes (working, counter, and reference electrodes), wherein the counter electrode is provided to balance the current generated by the species being measured at the working electrode. In the case of a glucose oxidase based glucose sensor, the species measured at the working electrode is $H_2O_2$. Glucose oxidase, GOX, catalyzes the conversion of oxygen and glucose to hydrogen peroxide and gluconate according to the following reaction:

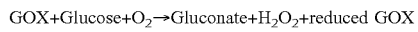

GOX+Glucose+$O_2$→Gluconate+$H_2O_2$+reduced GOX

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of working electrode and produces two protons (2H+), two electrons (2e−), and one oxygen molecule (O2). In such embodiments, because the counter electrode utilizes oxygen as an electron acceptor, the most likely reducible species for this system are oxygen or enzyme generated peroxide. There are two main pathways by which oxygen can be consumed at the counter electrode. These pathways include a four-electron pathway to produce hydroxide and a two-electron pathway to produce hydrogen peroxide. In addition to the counter electrode, oxygen is consumed by the reduced glucose oxidase within the enzyme domain. Therefore, due to the oxygen consumption by both the enzyme and the counter electrode, there is a net consumption of oxygen within the electrode system. Theoretically, in the domain of the working electrode there is significantly less net loss of oxygen than in the region of the counter electrode. In some electrochemical cell configurations, there is a close correlation between the ability of the counter electrode to maintain current balance and sensor function.

In general, in electrochemical sensors wherein an enzymatic reaction depends on oxygen as a co-reactant, depressed function or inaccuracy can be experienced in low oxygen environments, for example in vivo. Subcutaneously implanted devices are especially susceptible to transient ischemia that can compromise device function; for example, because of the enzymatic reaction required for an implantable amperometric glucose sensor, oxygen must be in excess over glucose in order for the sensor to effectively function as a glucose sensor. If glucose becomes in excess, the sensor turns into an oxygen sensitive device. In vivo, glucose concentration can vary from about one hundred times or more that of the oxygen concentration. Consequently, one limitation of prior art enzymatic-based electrochemical analyte sensors can be caused by oxygen deficiencies, which is described in more detail with reference to FIG. 3.

FIG. 1B is an exploded perspective view of one exemplary embodiment of an implantable glucose sensor that utilizes an electrode system 16b of the preferred embodiments. In this exemplary embodiment, a body with a sensing region 14 includes an electrode system 16b and sensor electronics, which are described in more detail with reference to FIG. 2.

In this embodiment, the electrode system 16b is operably connected to the sensor electronics (FIG. 2) and includes electroactive surfaces, which are covered by a membrane system 18. The membrane system 18 is disposed over the electroactive surfaces of the electrode system 16b and is substantially similar to the membrane system 18 described with reference to FIG. 1A.

In contrast to prior art electrochemical sensors, however, the preferred embodiments employ an electrode system 16b with sensing and oxygen-generating electrodes in relatively close proximity to each other, where one is used to generate oxygen, hereinafter referred to as the oxygen-generating electrode, and the other is used to sense an analyte or a product of a reaction indicative of the concentration of analyte, hereinafter referred to as the sensing electrode. The electrodes are preferably placed sufficiently close to one another such that the oxygen generated at the oxygen-generating electrode will diffuse to at least one oxygen-utilizing source, for example, an enzyme within the membrane system and/or to a counter electrode placed in proximity to the oxygen-generating electrode. The electrode systems of the preferred embodiments are described in more detail below, for example, with reference to FIGS. 4 to 6.

Figure 2:
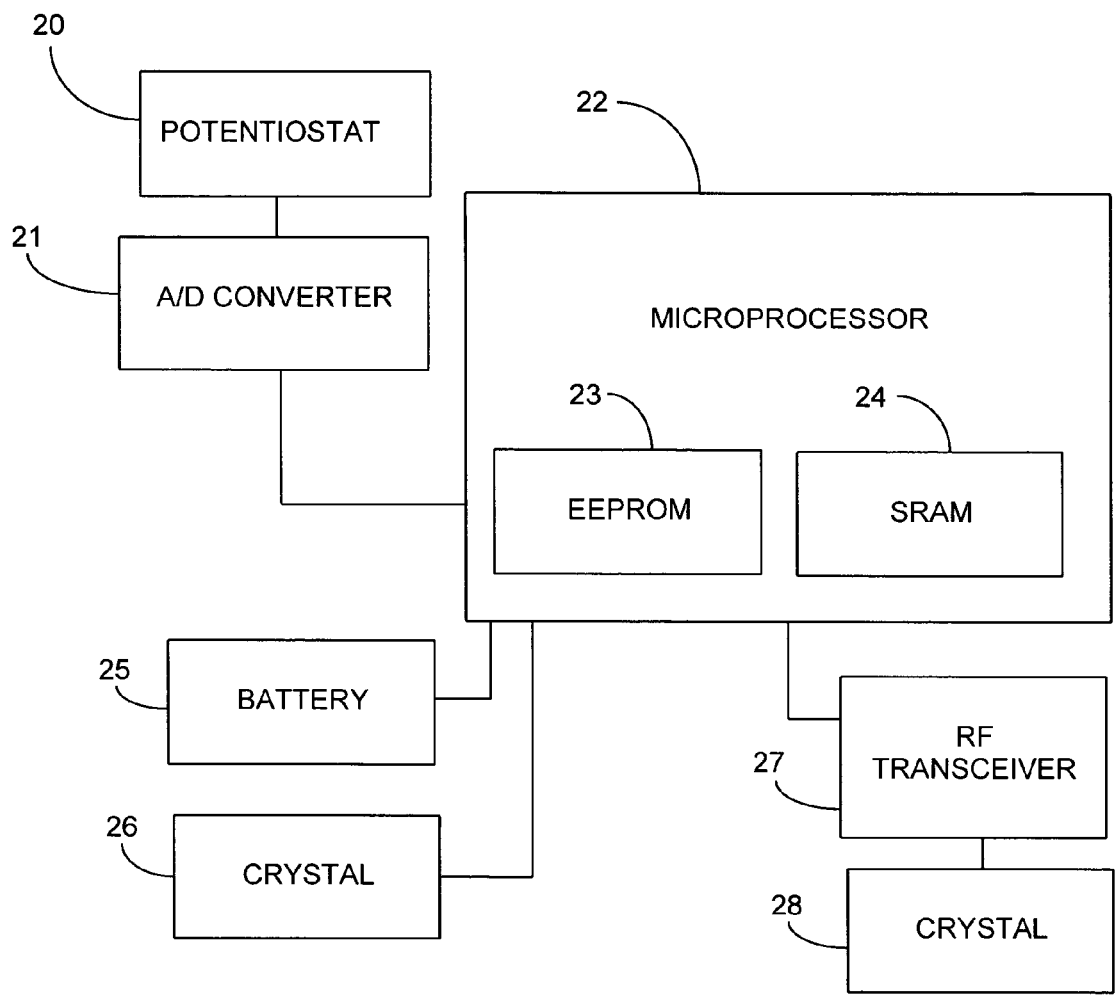
FIG. 2 is a block diagram that illustrates sensor electronics in one exemplary embodiment.

FIG. 2 is a block diagram that illustrates sensor electronics in one exemplary embodiment; one skilled in the art appreciates however a variety of sensor electronics configurations can be implemented with the preferred embodiments. In this embodiment, a potentiostat 20 is shown, which is operatively connected to electrode system 16 (FIGS. 1A and 1B) to obtain a current value, and includes a resistor (not shown) that translates the current into voltage. The A/D converter 21 digitizes the analog signal into "counts" for processing. Accordingly, the resulting raw data signal in counts is directly related to the current measured by the potentiostat.

A microprocessor 22 is the central control unit that houses EEPROM 23 and SRAM 24, and controls the processing of the sensor electronics. The alternative embodiments can utilize a computer system other than a microprocessor to process data as described herein. In some alternative embodiments, an application-specific integrated circuit (ASIC) can be used for some or all the sensor's central processing. EEPROM 23 provides semi-permanent storage of data, storing data such as sensor ID and necessary programming to process data signals (for example, programming for data smoothing such as described elsewhere herein). SRAM 24 is used for the system's cache memory, for example for temporarily storing recent sensor data.

The battery 25 is operatively connected to the microprocessor 22 and provides the necessary power for the sensor. In one embodiment, the battery is a Lithium Manganese Dioxide battery, however any appropriately sized and powered battery can be used. In some embodiments, a plurality of batteries can be used to power the system. Quartz Crystal 26 is operatively connected to the microprocessor 22 and maintains system time for the computer system.

The RF Transceiver 27 is operably connected to the microprocessor 22 and transmits the sensor data from the sensor to a receiver. Although a RF transceiver is shown here, some other embodiments can include a wired rather than wireless connection to the receiver. In yet other embodiments, the sensor can be transcutaneously connected via an inductive coupling, for example. The quartz crystal 28 provides the system time for synchronizing the data transmissions from the RF transceiver. The transceiver 27 can be substituted with a transmitter in one embodiment.

Figure 1B:
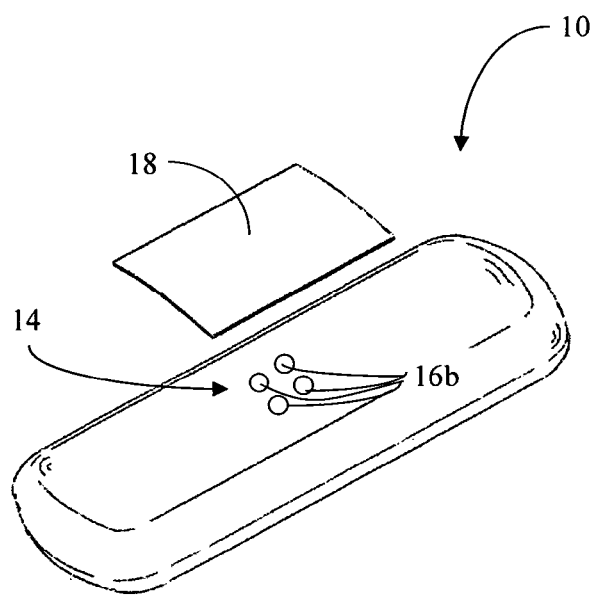

Although FIGS. 1 to 2 and associated text illustrate and describe an exemplary embodiment of an implantable glucose sensor, the electrode systems of the preferred embodiments described below can be implemented on any known electrochemical sensor, including U.S. Pat. No. 6,001,067 to Shults et al.; U.S. Pat. No. 6,702,857 to Brauker et al.; U.S. Pat. No. 6,212,416 to Ward et al.; U.S. Pat. No. 6,119,028 to Schulman et al.; U.S. Pat. No. 6,400,974 to Lesho; U.S. Pat. No. 6,595,919 to Berner et al.; U.S. Pat. No. 6,141,573 to Kurnik et al.; 6,122,536 to Sun et al.; European Patent Application EP 1153571 to Varall et al.; U.S. Pat. No. 6,512,939 to Colvin et al.; U.S. Pat. No. 5,605,152 to Slate et al.; U.S. Pat. No. 4,431,004 to Bessman et al.; U.S. Pat. No. 4,703,756 to Gough et al.; U.S. Pat. No. 6,514,718 to Heller et al.; U.S. Pat. No. to 5,985,129 to Gough et al.; WO Patent Application Publication No. 2004/021877 to Caduff; U.S. Pat. No. 5,494,562 to Maley et al.; U.S. Pat. No. 6,120,676 to Heller et al.; and U.S. Pat. No. 6,542,765 to Guy et al., co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA," the contents of each of which are incorporated herein by reference in their entireties.

Figure 3:
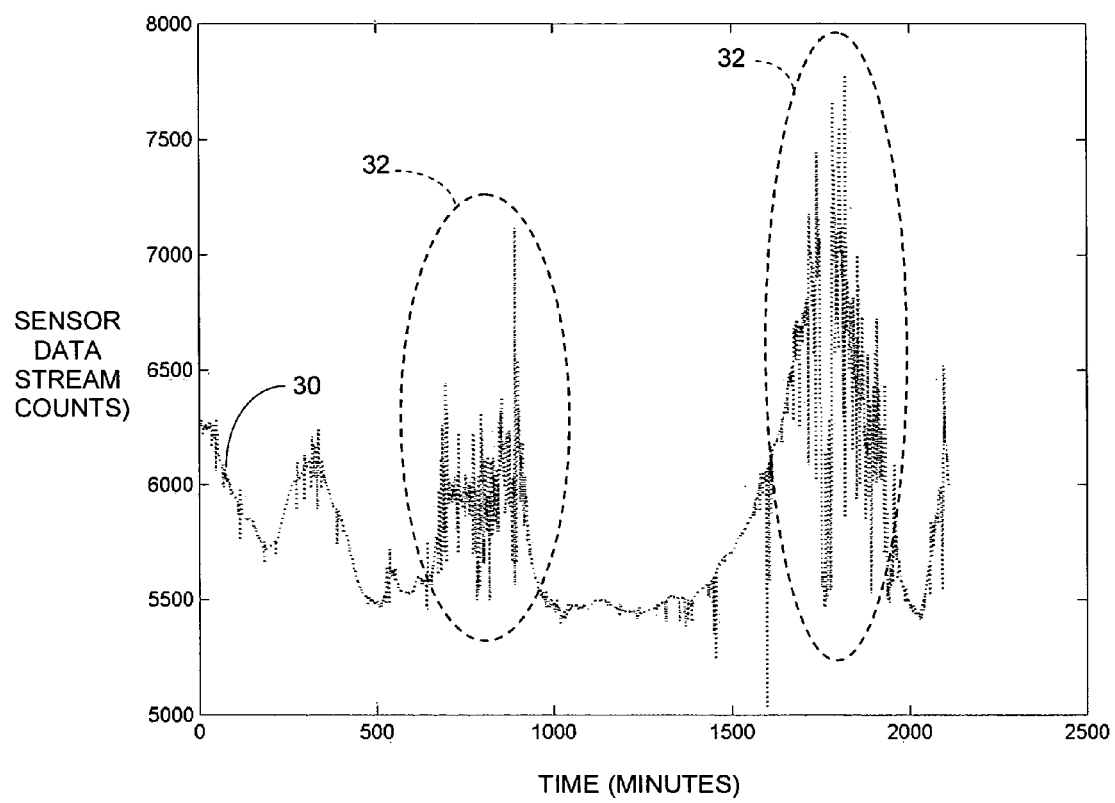
FIG. 3 is a graph that shows a raw data stream obtained from a glucose sensor such as described with reference to FIG. 1A.

FIG. 3 is a graph that shows a raw data stream obtained from a glucose sensor such as described with reference to FIG. 1A, including a prior art electrode system. The x-axis represents time in minutes. The y-axis represents sensor data in counts. In this example, sensor output in counts is transmitted every 30-seconds. The raw data stream 30 includes substantially smooth sensor output in some portions, however other portions exhibit erroneous or transient non-glucose related signal artifacts 32. Particularly, referring to the signal artifacts 32, it is believed that effects of local ischemia on prior art electrochemical sensors creates erroneous (non-glucose) signal values due to oxygen deficiencies either at the enzyme within the membrane system and/or at the counter electrode on the electrode surface.

When oxygen is deficient relative to the amount of glucose, then the enzymatic reaction is limited by oxygen rather than glucose. Thus, the output signal will be indicative of the oxygen concentration rather than the glucose concentration, producing erroneous signals. Additionally, when an enzymatic reaction is rate-limited by oxygen, glucose is expected to build up in the membrane because it is not completely catabolized during the oxygen deficit. When oxygen is again in excess, there is also excess glucose due to the transient oxygen deficit. The enzyme rate then speeds up for a short period until the excess glucose is catabolized, resulting in spikes of non-glucose related increased sensor output. Accordingly, because excess oxygen (relative to glucose) is necessary for proper sensor function, transient ischemia can result in a loss of signal gain in the sensor data.

In another situation, oxygen deficiency can be seen at the counter electrode when insufficient oxygen is available for reduction, which thereby affects the counter electrode in that it is unable to balance the current coming from the working electrode. When insufficient oxygen is available for the counter electrode, the counter electrode can be driven in its electrochemical search for electrons all the way to its most negative value, which can be ground or 0.0 V, which causes the reference to shift, reducing the bias voltage such as described in more detail below. In other words, a common result of ischemia is seen as a drop off in sensor current as a function of glucose concentration (for example, lower sensitivity). This happens because the working electrode no longer oxidizes all of the $H_2O_2$ arriving at its surface because of the reduced bias. In some extreme circumstances, an increase in glucose can produce no increase in current or even a decrease in current.

Transient ischemia can also occur at high glucose levels, wherein oxygen can become limiting to the enzymatic reaction, resulting in a non-glucose dependent downward trend in the data. In some situations, certain movements or postures taken by the patient can cause transient signal artifacts as blood is squeezed out of the capillaries resulting in local ischemia, and causing non-glucose dependent signal artifacts. In some situations, oxygen can also become transiently limited due to contracture of tissues around the sensor interface. This is similar to the blanching of skin that can be observed when one puts pressure on it. Under such pressure, transient ischemia can occur in both the epidermis and subcutaneous tissue. Transient ischemia is common and well tolerated by subcutaneous tissue. However, such ischemic periods can cause an oxygen deficit in implanted devices that can last for many minutes or even an hour or longer.

Although some examples of the effects of transient ischemia on a prior art glucose sensor are described above, similar effects can be seen with analyte sensors that use alternative catalysts to detect other analytes, for example, amino acids (amino acid oxidase), alcohol (alcohol oxidase), galactose (galactose oxidase), lactate (lactate oxidase), cholesterol (cholesterol oxidase), or the like.

Electrode Systems of the Preferred Embodiments

In order to overcome the effects of transient ischemia, the preferred embodiments employ an electrode system with at least two electrodes in relatively close proximity to each other, wherein at least one electrode is configured to generate oxygen, also referred to as the oxygen-generating electrode, and at least one other electrode is configured to sense an analyte or a product of a reaction indicative of the concentration of analyte, also referred to as the sensing electrode. The oxygen generated by the oxygen-generating electrode is available to the catalyst within a membrane system and/or the counter electrode, thereby enabling the electrochemical sensors of the preferred embodiments to function even during ischemic conditions.

In some embodiments, the electrode system of the preferred embodiments is configured with two working electrodes and one reference electrode, wherein one of the working electrodes is configured as an oxygen-generating electrode. In another embodiment, the electrode system of the preferred embodiments is configured with two working electrodes, one reference electrode, and one counter electrode, wherein one of the working electrodes is configured as an oxygen-generating electrode. In some alternative embodiments, additional electrodes (in addition to the above-described embodiments) can be provided, for example, an additional working electrode configured to measure an additional analyte (for example, oxygen) and/or an additional working electrode configured as a baseline-subtracting electrode (for example, without an active enzyme disposed there over).

When two working electrodes are in relatively close proximity to each other, some of the hydrogen peroxide normally sensed at the sensing electrode can react instead at the oxygen-generating electrode, causing a reduction in signal at the sensing electrode. However, this reduction in signal at the sensing electrode will be a stable reduction in signal strength causing a decreased but linear response to hydrogen peroxide concentration. In some embodiments, the distances between the sensing and oxygen-generating electrodes can be adjusted to optimize the oxygen availability while minimizing the reduction in signal strength. In some embodiments, it can be advantageous to utilize a different metal for the oxygen-producing electrode than the sensing electrode in order to produce oxygen at a lower potential. For example, the electrodes can be chosen from glassy carbon, gold, platinum, palladium, nickel, silver, copper, lead, zinc, and/or silver/carbon; however, other electrode materials can also be used.

The working electrodes can comprise any electrode configuration and are preferably arranged in proximity, such as described in more detail above. For example, the electrodes can be configured in a spiral, concentric, adjacent, interdigitated, sandwiched, or any other known pattern. Furthermore, the working electrodes can be formed in any known manner including but not limited to thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, laser cutting, for example.

Figure 4:
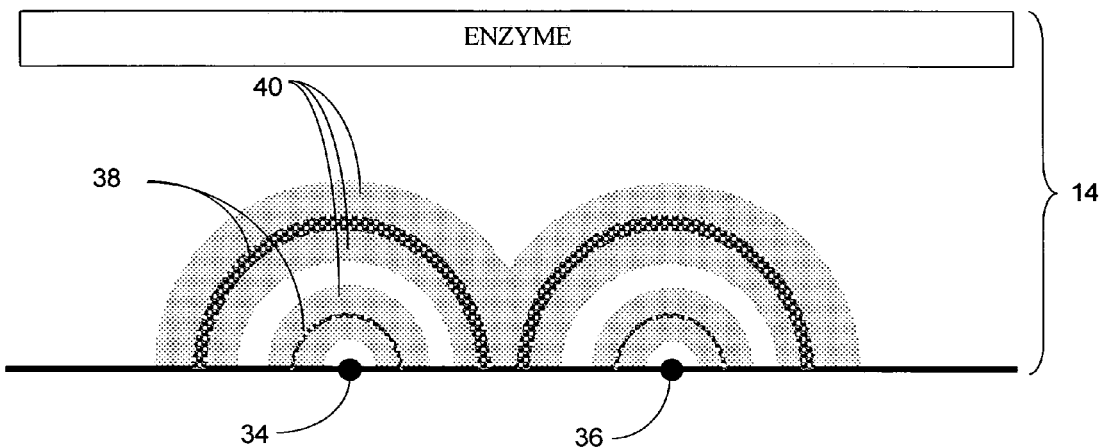
FIG. 4 is a side schematic illustration of a portion of the sensing region of an electrochemical sensor of the preferred embodiments, showing sensing and oxygen-generating electrodes placed in relatively close proximity to each other.

FIG. 4 is a side schematic illustration of a portion of the sensing region of an electrochemical sensor of the preferred embodiments, showing sensing and oxygen-generating electrodes placed in relatively close proximity to each other. The sensing region 14 includes an enzyme (within a membrane system) that catalyzes the reaction of an analyte and oxygen, and further includes electroactive surfaces with at least a sensing electrode 34 and an oxygen-generating electrode 36.

FIG. 4 further illustrates the resulting hydrogen peroxide and oxygen concentrations in the local environment, 38 and 40, respectively. Namely, hydrogen peroxide 38 is oxidized at both the sensing electrode 34 and the oxygen-generating electrode 36 and diffuses into the local environment of the electrode. Similarly, oxygen 40 is produced at both the sensing electrode 34 and the oxygen-generating electrode 36 and diffuses into the local environment of the electrode. Because oxidation of $H_2O_2$ by the working electrode is balanced by reduction of ambient oxygen, enzyme generated $H_2O_2$, or other reducible species at the counter electrode (not shown), an excess of oxygen will be produced by the auxiliary oxygen-generating electrode. The oxygen-generating electrode 36 is set at a potential that oxidizes water ($H_2O$), or other reducible species, at its surface, in order to generate oxygen.

The oxygen 40 diffuses at least in part upward toward the enzyme, to be used in the enzymatic reaction therein. Additionally, the oxygen 40 can diffuse at least in part over to a counter electrode (if one is placed within the local oxygen diffusion environment 40 of one of the electrodes). The configurations of the working electrodes of preferred embodiments can be applied to a variety of electrode configurations, including reference, counter, and/or additional working electrodes.

Referring now to the placement of the oxygen-generating electrode within the sensing region, it is believed that local generation of oxygen from an electrode is dependent upon the electroactive surface area (of the one or more oxygen-sensing electrodes) and/or the applied voltage (of the one or more oxygen-sensing electrodes), for example. Thus, the placement of the oxygen-generating electrode can depend upon the electroactive surface area, the applied voltage, the location of the sensing electrode, and/or the location of the counter electrode (if applicable). For example, increasing the applied voltage of the oxygen-generating electrode(s) increases the amount of oxygen generated, thereby enabling the oxygen-generating electrodes to be located farther from the sensing electrode(s) than other relatively smaller electrodes. In both of the above-cited examples, it is preferable that oxygen generated by of the oxygen-generating electrode(s) diffuses to the enzyme, and more preferably to the portion of the enzyme located substantially directly above the sensing electrode. Additionally or alternatively, in embodiments wherein the electrode system includes a counter electrode, the oxygen-generating electrode(s) is preferably located in such proximity to the counter electrode so as to aid in compensating for the reduction of ambient oxygen at the surface of the counter electrode.

In some embodiments, the spacing between the sensing and oxygen-generating electrodes is from about 0.5 microns or less to about 1000 microns or more. In some embodiments, the spacing between the sensing and oxygen-generating electrodes is from about 1, 2, 3, 4, 5, 6, 7, 8, 9, or 10 microns to about 100, 200, 300, 400, 500, 600, 700, 800, or 900 microns. In some embodiments, the spacing between the sensing and oxygen-generating electrodes is from about 15, 20, 25, 30, 35, 40, or 45 microns to about 55, 60, 65, 70, 75, 80, 85, 90, or 95 microns. In some embodiments, the spacing between the sensing and oxygen-generating electrodes is about 50 microns.

Figure 5:
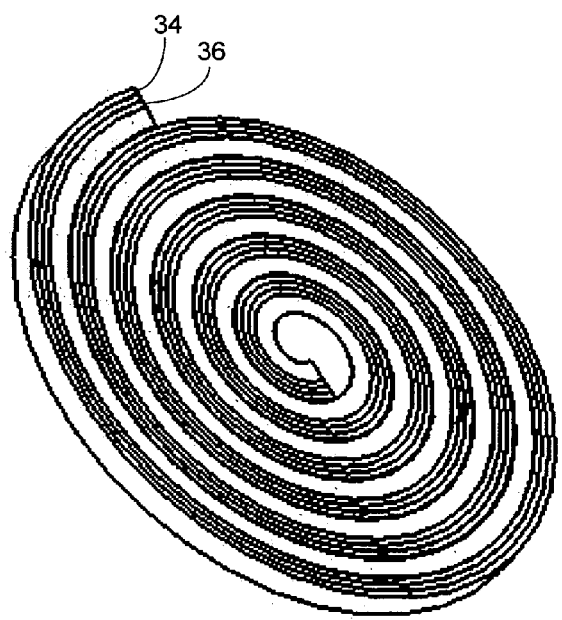
FIG. 5 is perspective view of an electrode system in an alternative embodiment, wherein the electrodes comprise a spiral configuration with a sensing electrode in close proximity to an oxygen-generating electrode.

FIG. 5 is perspective view of an electrode system in an alternative embodiment, wherein the electrodes comprise a spiral configuration with the sensing electrode 34 in close proximity to the oxygen-generating electrode 36 (with insulating material therebetween). In some embodiments, the spiral configuration further includes a reference and/or counter electrode included within the spiral configuration. See co-pending U.S. patent application Ser. No. 10/896,637, filed on even date herewith, and entitled, "ROLLED ELECTRODE ARRAY AND ITS METHOD FOR MANUFACTURE," which is incorporated herein by reference in its entirety. This configuration is particularly advantageous in that the oxygen-generating electrode(s) substantially surrounds the sensing electrode(s) (and/or the counter electrode) in such close proximity so as to produce a local oxygen diffusion environment that substantially surrounds the sensing electrode(s) (and/or counter electrode); thus utilizing the excess oxygen generated efficiently.

Figure 6:
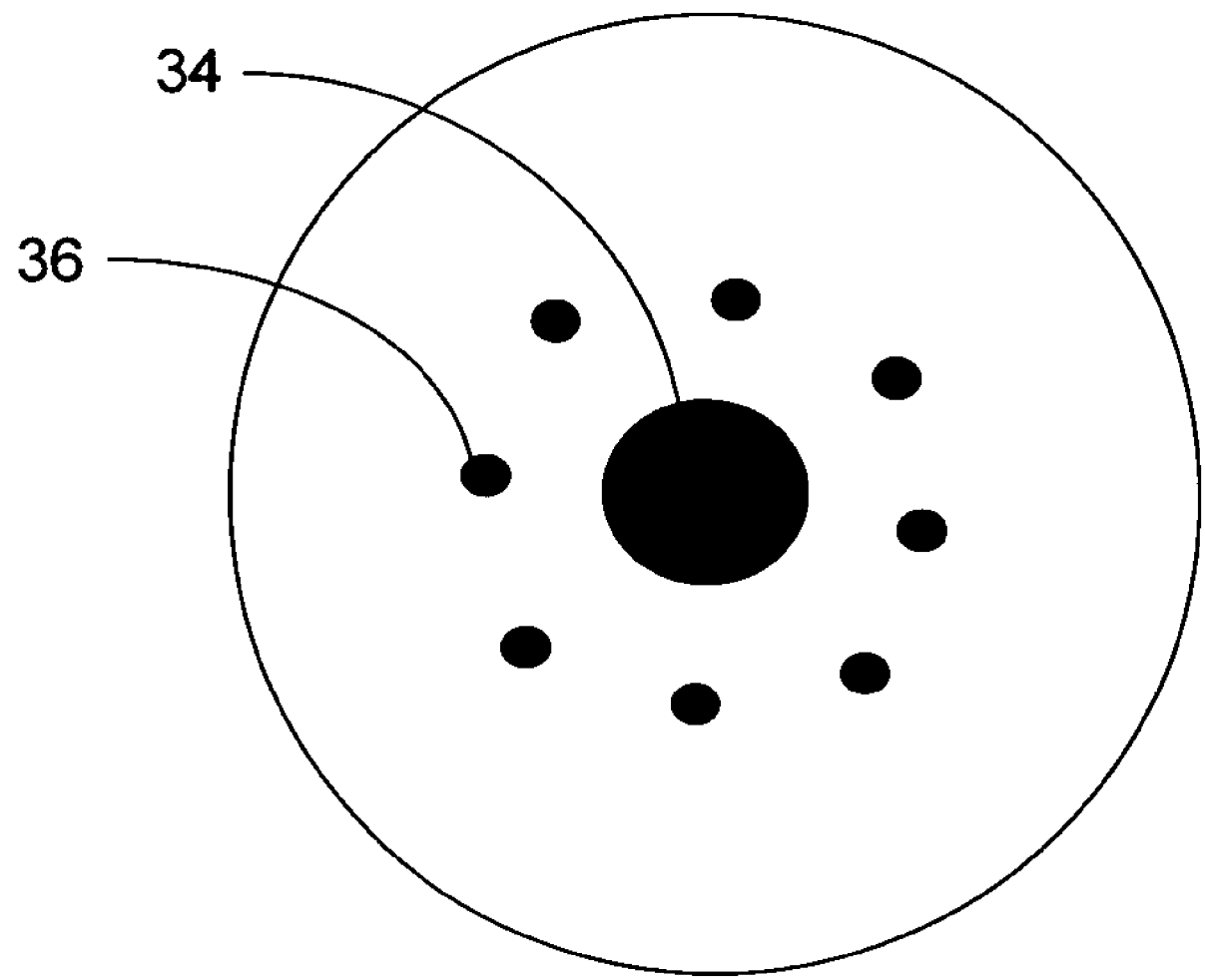
FIG. 6 is a top view of another alternative embodiment, wherein the electrode system comprises an array of oxygen-generating electrodes that encircle a sensing electrode.

FIG. 6 is a top view of another alternative embodiment, wherein the electrode system comprises an array of oxygen-generating electrodes 36 that encircle the sensing electrode 34. In one implementation of this embodiment, the array of oxygen-generating electrodes can optionally extend higher than the sensing electrode toward the enzyme layer, thereby focusing the generating oxygen toward the enzyme. Additionally, if the array of oxygen-generating electrodes 36 extends upward, like posts, then a substantial portion of their surface area (for example, circumference) can be covered with an insulator that encourages transport of water but not hydrogen peroxide, such as silicone, for example, to decrease their reactivity with hydrogen peroxide.

Figure 7:
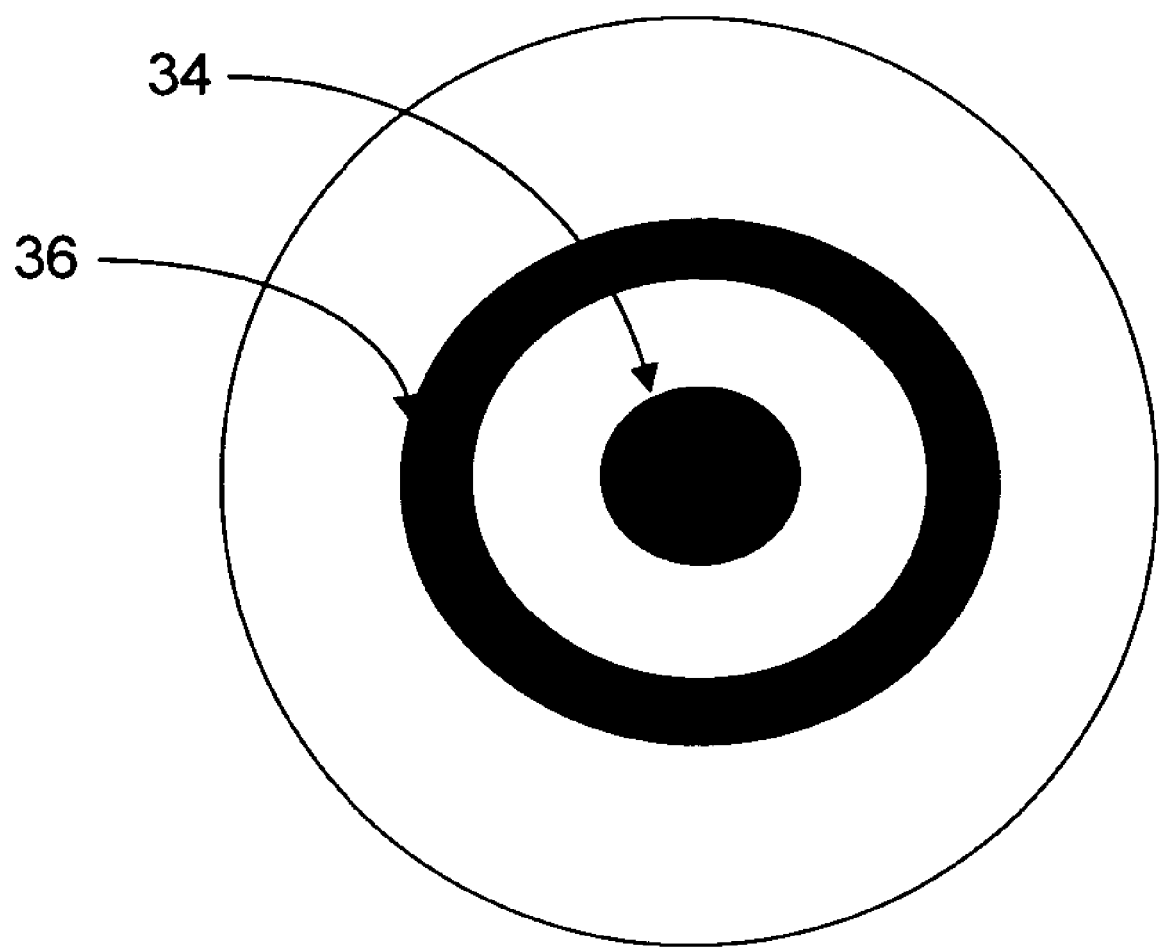
FIG. 7 is a top view of yet another alternative embodiment, wherein the electrode system comprises a concentric configuration.

FIG. 7 is a top view of yet another alternative embodiment, wherein the electrode system comprises a concentric configuration including an oxygen-generating electrode 36 encircling the sensing electrode 34. Concentric placement of the oxygen-generating electrode can be advantageous due to its symmetry and accurate spacing control, as appreciated by one skilled in the art as advantageous in electrochemistry.

Figure 8:
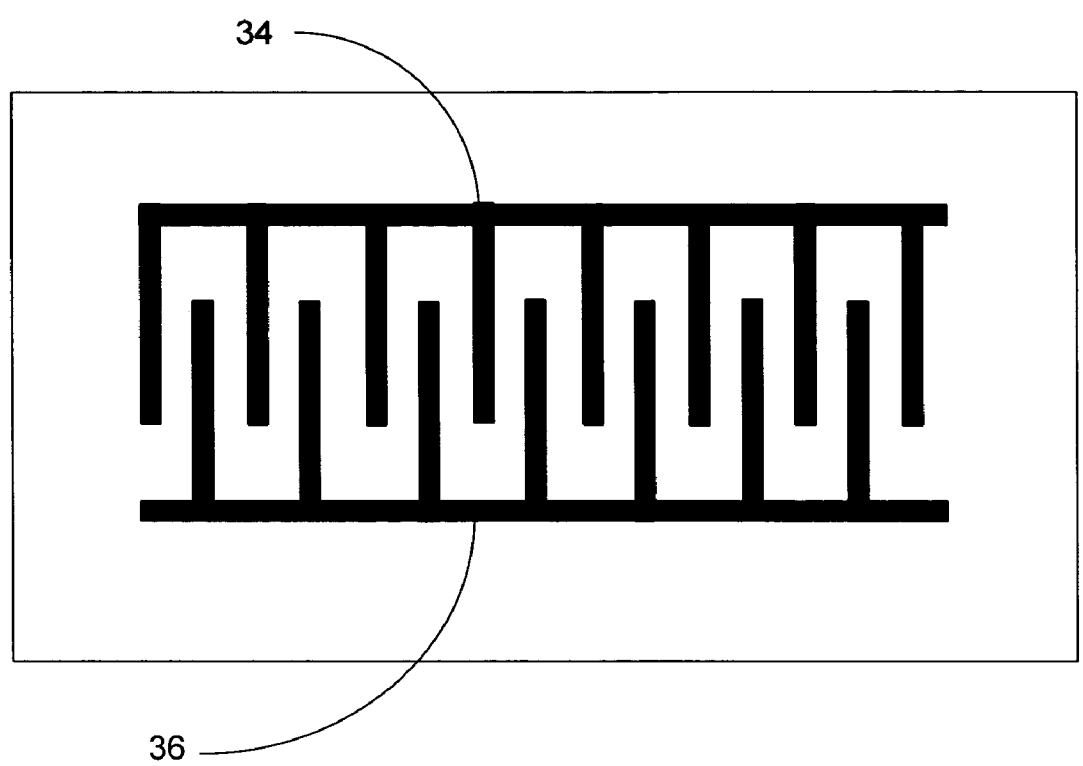
FIG. 8 is a top view of yet another alternative embodiment, wherein the electrode system comprises an interdigitated configuration.

FIG. 8 is a top view of yet another alternative embodiment, wherein the electrode system comprises an interdigitated configuration including oxygen-generating electrodes 36 encircling sensing electrodes 34. This interdigitated electrode configuration enables a proximity of the sensing and oxygen-generating electrodes that is believed to optimize efficient utilization of the oxygen at the sensing electrode.

The above-described illustrations show only the working electrode portion (for example, sensing electrode with oxygen-generating electrode(s)) of an electrode system. Counter electrodes and/or reference electrodes can be implemented as is appreciated by one skilled in the art. One example of an electrode system including counter and reference electrodes is described in more detail in co-pending U.S. Published Patent Application 2003/0032874 to Rhodes et al., the contents of which are incorporated herein by reference in their entirety. In embodiments wherein the electrode system comprises a counter electrode, the oxygen-generating electrode can also be located in such proximity to the counter electrode to help compensate for the reduction of ambient oxygen at the surface of the counter electrode, such as described elsewhere in more detail.

Accordingly, the electrode systems of preferred embodiments include sensing and oxygen-generating working electrodes configured produce oxygen for the enzyme within the membrane system and/or at the counter electrode.

Methods and devices that are suitable for use in conjunction with aspects of the preferred embodiments are disclosed in co-pending U.S. patent application Ser. No. 10/842,716, filed May 10, 2004 and entitled, "MEMBRANE SYSTEMS INCORPORATING BIOACTIVE AGENTS"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR MEMBRANE SYSTEM"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. application Ser. No. 60/489,615 filed Jul. 23, 2003 and entitled "ROLLED ELECTRODE ARRAY AND ITS METHOD FOR MANUFACTURE"; U.S. appl. Ser. No. 60/490,010 filed Jul. 25, 2003 and entitled "INCREASING BIAS FOR OXYGEN PRODUCTION IN AN ELECTRODE ASSEMBLY"; U.S. application Ser. No. 60/490,009 filed Jul. 25, 2003 and entitled "OXYGEN ENHANCING ENZYME MEMBRANE FOR ELECTROCHEMICAL SENSORS"; U.S. application Ser. No. 60/490,007 filed Jul. 25, 2003 and entitled "OXYGEN-GENERATING ELECTRODE FOR USE IN ELECTROCHEMICAL SENSORS"; U.S. application Ser. No. 10/896,637 filed on even date herewith and entitled "ROLLED ELECTRODE ARRAY AND ITS METHOD FOR MANUFACTURE"; U.S. application Ser. No. 10/896,772 filed on even date herewith and entitled "INCREASING BIAS FOR OXYGEN PRODUCTION IN AN ELECTRODE ASSEMBLY"; U.S. application Ser. No. 10/896,639 filed on even date herewith and entitled "OXYGEN ENHANCING ENZYME MEMBRANE FOR ELECTROCHEMICAL SENSORS"; U.S. application Ser. No. 10/897,312 filed on even date herewith and entitled "ELECTRODE SYSTEMS FOR ELECTROCHEMICAL SENSORS". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. An electrochemical sensor for determining a presence or a concentration of an analyte in a fluid, the sensor comprising:
   a membrane system comprising an enzyme that reacts with the analyte;
   a first working electrode comprising a conductive material, wherein the first working electrode is configured to measure a product of the reaction of the enzyme with the analyte; and
   an auxiliary electrode comprising a conductive material, wherein the auxiliary electrode is configured to generate oxygen; and a counter electrode comprising a conductive material, wherein the counter electrode is configured to reduce oxygen so as to balance current being generated by the first working electrode, wherein the auxiliary electrode is located at a proximity to the counter electrode such that oxygen generated at the auxiliary electrode diffuses to the counter electrode to be reduced thereby.

2. The electrochemical sensor of claim 1, wherein a distance between the auxiliary electrode and the counter electrode is from about 0.5 microns to about 1000 microns.

3. The electrochemical sensor of claim 1, wherein a distance between the auxiliary electrode and the counter electrode is from about 10 microns to about 100 microns.

4. The electrochemical sensor of claim 1, wherein a distance between the auxiliary electrode and the counter electrode is about 50 microns.

5. The electrochemical sensor of claim 1, wherein at least one of the working electrode and the counter electrode is configured in a pattern selected from the group consisting of spiral, concentric, adjacent, interdigitated, and sandwiched.

6. The electrochemical sensor of claim 1, wherein at least one of the working electrode and the counter electrode is formed by a process selected from the group consisting of thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, and laser cutting.

7. The electrochemical sensor of claim 1, wherein the first working electrode comprises a sensing electrode, and wherein the auxiliary electrode comprises an oxygen-generating electrode.

8. The electrochemical sensor of claim 1, further comprising an additional working electrode comprising a conductive material, wherein the additional working electrode is configured to measure an additional analyte or is configured to function as a baseline-subtracting electrode.

9. The electrochemical sensor of claim 1, further comprising at least one additional working electrode comprising a conductive material and configured to generate oxygen.

10. The electrochemical sensor of claim 9, wherein the additional working electrode is configured to substantially surround the first working electrode.

11. The electrochemical sensor of claim 1, wherein the conductive material in the auxiliary electrode is different than the conductive material in the first working electrode, wherein the auxiliary electrode is configured to generate oxygen at a potential lower than the potential at which the first working electrode measures the product of the reaction of the enzyme with the analyte.

12. The electrochemical sensor of claim 1, wherein the auxiliary electrode is configured to generate oxygen at least partially by oxidation of at least one of water and an electroactive species other than said product of the reaction of the enzyme with the analyte.

13. The electrochemical sensor of claim 1, wherein the membrane system is configured such that the analyte diffuses to the enzyme over both the first working electrode and the auxiliary electrode.

14. A method for generating oxygen for use at an electrochemical analyte sensor, the method comprising:

providing a membrane system comprising an enzyme that reacts with the analyte;

providing a first working electrode comprising a conductive material;

measuring a product of a reaction of the enzyme with the analyte at the first working electrode, wherein a concentration of the product is indicative of a concentration of the analyte;

providing an auxiliary electrode comprising a conductive material; and generating oxygen at the auxiliary electrode, wherein the auxiliary electrode is configured such that the oxygen generated at the auxiliary electrode diffuses toward the enzyme at a location substantially above the first working electrode, and wherein the membrane system, first working electrode, and auxiliary electrode are configured such that said product of the reaction of the enzyme with the analyte diffuses into a local environment of the first working electrode and the auxiliary electrode.

15. The method of claim 14, wherein the enzyme is selected from the group consisting of glucose oxidase, amino acid oxidase, alcohol oxidase, galactose oxidase, lactate oxidase, and cholesterol oxidase.

16. The method of claim 14, wherein the analyte is selected from the group consisting of glucose, amino acid, alcohol, galactose, lactate, and cholesterol.

17. The method of claim 14, wherein the conductive material in the auxiliary electrode is different than the conductive material in the first working electrode, wherein generating oxygen at the auxiliary electrode comprises setting the potential of the auxiliary electrode lower than the potential at which the first working electrode measures the product of the reaction of the enzyme with the analyte.

18. The electrochemical sensor of claim 14, wherein generating oxygen at the auxiliary electrode at least partially comprises oxidizing at least one of water and an electroactive species other than said product of the reaction of the enzyme with the analyte.

19. The electrochemical sensor of claim 14, wherein the membrane system is configured such that the analyte diffuses to the enzyme over both the first working electrode and the auxiliary electrode.

20. A method for generating oxygen for use at an electrochemical analyte sensor, the method comprising:

providing an electrochemical sensor comprising a sensing electrode and an auxiliary electrode;

measuring an analyte at the sensing electrode; and generating oxygen at the auxiliary electrode, wherein the electrochemical sensor comprises a counter electrode, and wherein the oxygen generated by the auxiliary electrode diffuses to the counter electrode.

21. The method of claim 20, wherein generating oxygen at the auxiliary electrode comprises setting the potential of the auxiliary electrode lower than the potential at which sensing electrode measures the analyte.

22. An electrochemical sensor for determining a presence or a concentration of an analyte in a fluid, the sensor comprising:

a membrane system comprising an enzyme that reacts with the analyte;

a first working electrode comprising a conductive material, wherein the first working electrode is configured to measure a product of the reaction of the enzyme with the analyte; and an auxiliary electrode comprising a conductive material, wherein the auxiliary electrode is configured to generate oxygen, wherein the auxiliary electrode is located at a proximity to the first working electrode such that oxygen generated at the auxiliary electrode diffuses to the enzyme at a location substantially above the first working electrode, and wherein the membrane system, first working electrode, and auxiliary electrode are configured such that said product of the reaction of the enzyme with the analyte diffuses into a local environment of the first working electrode and the auxiliary electrode, and wherein the conductive material in the auxiliary electrode is different than the conductive material in the first working electrode, wherein the auxiliary electrode is configured to generate oxygen at a potential lower than the potential at which the first working electrode measures the product of the reaction of the enzyme with the analyte.

23. The electrochemical sensor of claim 22, wherein a distance between the first working electrode and the auxiliary electrode is from about 0.5 to about 1000 microns.

24. The electrochemical sensor of claim 22, wherein a distance between the first working electrode and the auxiliary electrode is from about 10 to about 100 microns.

25. The electrochemical sensor of claim 22, wherein a distance between the first working electrode and the auxiliary electrode is about 50 microns.

26. The electrochemical sensor of claim 22, wherein at least one of the first working electrode and the auxiliary electrode is configured in a pattern selected from the group consisting of spiral, concentric, adjacent, interdigitated, and sandwiched.

27. The electrochemical sensor of claim 22, wherein at least one of the first working electrode and the auxiliary electrode is formed by a process selected from the group consisting of thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, and laser cutting.

28. The electrochemical sensor of claim 22, further comprising a counter electrode, wherein the counter electrode is situated in proximity to the auxiliary electrode such that oxygen generated by the auxiliary electrode diffuses to the counter electrode.

29. The electrochemical sensor of claim 22, further comprising at least one additional auxiliary electrode comprising a conductive material and configured to generate oxygen.

30. The electrochemical sensor of claim 29, wherein the additional auxiliary electrode is configured to substantially surround the first working electrode.

31. The electrochemical sensor of claim 22, further comprising an additional working electrode comprising a conductive material, wherein the additional working electrode is configured to measure an additional analyte or is configured to function as a baseline-subtracting electrode.

32. An electrochemical sensor for determining a presence or a concentration of an analyte in a fluid, the sensor comprising:
a membrane system comprising an enzyme that reacts with the analyte;
a first working electrode comprising a conductive material, wherein the first working electrode is configured to measure a product of the reaction of the enzyme with the analyte; and
an auxiliary electrode comprising a conductive material, wherein the auxiliary electrode is configured to generate oxygen,
wherein the auxiliary electrode is located at a proximity to the first working electrode such that oxygen generated at the auxiliary electrode diffuses to the enzyme at a location substantially above the first working electrode, and wherein the membrane system, first working electrode, and auxiliary electrode are configured such that said product of the reaction of the enzyme with the analyte diffuses into a local environment of the first working electrode and the auxiliary electrode, and wherein the auxiliary electrode is configured to generate oxygen at least partially by oxidation of at least one of water and an electroactive species other than said product of the reaction of the enzyme with the analyte.

33. The electrochemical sensor of claim 32, wherein a distance between the first working electrode and the auxiliary electrode is from about 0.5 to about 1000 microns.

34. The electrochemical sensor of claim 32, wherein a distance between the first working electrode and the auxiliary electrode is from about 10 to about 100 microns.

35. The electrochemical sensor of claim 32, wherein a distance between the first working electrode and the auxiliary electrode is about 50 microns.

36. The electrochemical sensor of claim 32, wherein at least one of the first working electrode and the auxiliary electrode is configured in a pattern selected from the group consisting of spiral, concentric, adjacent, interdigitated, and sandwiched.

37. The electrochemical sensor of claim 32, wherein at least one of the first working electrode and the auxiliary electrode is formed by a process selected from the group consisting of thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, and laser cutting.

38. The electrochemical sensor of claim 32, further comprising a counter electrode, wherein the counter electrode is situated in proximity to the auxiliary electrode such that oxygen generated by the auxiliary electrode diffuses to the counter electrode.

39. The electrochemical sensor of claim 32, further comprising at least one additional auxiliary electrode comprising a conductive material and configured to generate oxygen.

40. The electrochemical sensor of claim 39, wherein the additional auxiliary electrode is configured to substantially surround the first working electrode.

41. The electrochemical sensor of claim 32, further comprising an additional working electrode comprising a conductive material, wherein the additional working electrode is configured to measure an additional analyte or is configured to function as a baseline-subtracting electrode.

42. An electrochemical sensor for determining a presence or a concentration of an analyte in a fluid, the sensor comprising:
a membrane system comprising an enzyme that reacts with the analyte;
a first working electrode comprising a conductive material, wherein the first working electrode is configured to measure a product of the reaction of the enzyme with the analyte; and
an auxiliary electrode comprising a conductive material, wherein the auxiliary electrode is configured to generate oxygen,
wherein the auxiliary electrode is located at a proximity to the first working electrode such that oxygen generated at the auxiliary electrode diffuses to the enzyme at a location substantially above the first working electrode, and wherein the membrane system, first working electrode, and auxiliary electrode are configured such that said product of the reaction of the enzyme with the analyte diffuses into a local environment of the first working electrode and the auxiliary electrode, and wherein the membrane system is configured such that the analyte diffuses to the enzyme over both the first working electrode and the auxiliary electrode.

43. The electrochemical sensor of claim 42, wherein a distance between the first working electrode and the auxiliary electrode is from about 0.5 to about 1000 microns.

44. The electrochemical sensor of claim 42, wherein a distance between the first working electrode and the auxiliary electrode is from about 10 to about 100 microns.

45. The electrochemical sensor of claim 42, wherein a distance between the first working electrode and the auxiliary electrode is about 50 microns.

46. The electrochemical sensor of claim 42, wherein at least one of the first working electrode and the auxiliary electrode is configured in a pattern selected from the group consisting of spiral, concentric, adjacent, interdigitated, and sandwiched.

47. The electrochemical sensor of claim 42, wherein at least one of the first working electrode and the auxiliary electrode is formed by a process selected from the group consisting of thick film printing, screen printing, lithography, letter press printing, vapor deposition, spray coating, pad printing, ink jet printing, laser jet printing, roller coating, vacuum deposition, thin film deposition, sputtering, evaporation, glow discharge methods, gluing, epoxy bonding, casting, rolling, machining, and laser cutting.

48. The electrochemical sensor of claim 42, further comprising a counter electrode, wherein the counter electrode is situated in proximity to the auxiliary electrode such that oxygen generated by the auxiliary electrode diffuses to the counter electrode.

49. The electrochemical sensor of claim 42, further comprising at least one additional auxiliary electrode comprising a conductive material and configured to generate oxygen.

50. The electrochemical sensor of claim 49, wherein the additional auxiliary electrode is configured to substantially surround the first working electrode.

51. The electrochemical sensor of claim 42, further comprising an additional working electrode comprising a conductive material, wherein the additional working electrode is configured to measure an additional analyte or is configured to function as a baseline-subtracting electrode.

* * * * *